United States Patent [19]

Brendel et al.

[11] Patent Number: 5,382,585
[45] Date of Patent: Jan. 17, 1995

[54] PYRIMIDOFUROXANS, THEIR PREPARATION AND THEIR USE

[75] Inventors: Joachim Brendel, Frankfurt am Main; Karl Schönafinger, Alzenau; Helmut Bohn, Schöneck, all of Germany

[73] Assignee: Cassella AG, Frankfurt am Main, Germany

[21] Appl. No.: 66,904

[22] Filed: May 25, 1993

[30] Foreign Application Priority Data

Jun. 10, 1992 [DE] Germany .............................. 4218979

[51] Int. Cl.⁶ ................. A61K 31/495; A61K 31/50; C07D 413/00; C07D 413/02
[52] U.S. Cl. .................... 514/253; 514/258; 544/118; 544/254
[58] Field of Search ............... 544/118, 254; 514/253, 514/258

[56] References Cited

U.S. PATENT DOCUMENTS 4,356,178 10/1982 Schonafinger et al. ............ 424/248
4,416,893 11/1983 Schonafinger et al. ............ 424/272

FOREIGN PATENT DOCUMENTS 0054872 12/1981 European Pat. Off. .
0038438  6/1983 European Pat. Off. .
0054873 10/1984 European Pat. Off. .
0431944  6/1991 European Pat. Off. .
2703369  7/1977 Germany .

OTHER PUBLICATIONS

Yoneda et al., Journal of Heterocyclic Chemistry, 10(3), 415, Jun. 1973.
Yoneda et al., Heterocycles, 15(1), 341–344, 1981.
Arzneim.-Forschung/Drug Res. 33(I), Nr. 6 (1983), p. 803, Binder et al.
J. Chem. Soc. Parkin Trans I (1976), p. 1327, Nutiu et al.
J. Org. Chem. 1986, p. 2086, Temple et al.
J. Chem. Soc., Chem. Commun., 1982, pp. 267 and 60, Tennant et al.
Heterocycles, vol. 5, No. 2, 1975, pp. 113–116, Yoneda et al.
J. Het. Chem. 1973, p. 993.

*Primary Examiner*—Mukund J. Shah
*Assistant Examiner*—Matthew V. Grumbling
*Attorney, Agent, or Firm*—Perman & Green

[57] ABSTRACT

The present invention relates to pyrimidofuroxans of the general formula I

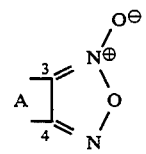

in which A denotes

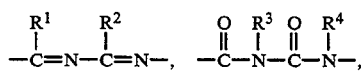

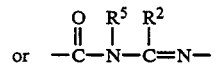

where in each case the nitrogen atom is bonded via the C-4 and the carbon atom via the C-3 of the furoxan ring and the R radicals are defined as indicated in Claim 1, processes for their preparation and their use for the control and prevention of disorders of the cardiovascular system, in particular for the control and prevention of angina pectoris, and for the treatment of erectile dysfunctions.

10 Claims, No Drawings

PYRIMIDOFUROXANS, THEIR PREPARATION AND THEIR USE

BACKGROUND OF THE INVENTION

1. Field of the Invention

The present invention relates to pyrimidofuroxans and their use as pharmacological active compounds.

2. Discussion of the Prior Art

A number of compounds of the pyrimidofuroxan class are already known and described, in particular, in the scientific literature. (see, for example, Arzneim.-Forsch. 33 (1983) 803; J. Chem. Soc., Perkin Trans I 1976, 1327; J. Org. Chem. 1968, 2086; J. Chem. Soc., Chem. Comm. 1982, 267 and 60; Heterocycles 1975, 113; J. Het. Chem. 1973, 993 and German Offenlegungsschrift 2,703,369). As pharmacological active compounds, to date only uncondensed, substituted furoxans have been described (see, for example: EP-B 0,038,438, EP-B 0,054,872 and EP-B 0,054,873).

SUMMARY OF THE INVENTION

The present invention relates to pyrimidofuroxans of the general formula I

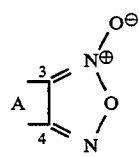

in which

A denotes

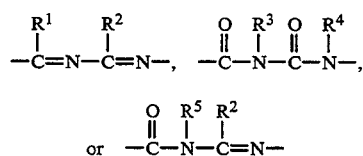

where in each case the nitrogen atom is bonded via C-4 and the carbon atom is bonded via C-3 of the furoxan ring;

$R^1$ denotes —$NHR^6$, —$NR^7R^8$, —NX, —NHOH, —$NH(CH_2)_nY$, —$N[(CH_2)_nY]_2$ or —$NH(CH_2)_mZ$;

$R^2$ denotes hydrogen or —$OR^7$;

$R^3$ denotes ($C_2$–$C_4$)-alkyl;

$R^4$ denotes hydrogen, ($C_1$–$C_6$)-alkyl, ($C_5$–$C_7$)-cycloalkyl, —$CH_2Z$, —$CH_2COOR^7$, —$CH_2CONR^7R^8$, —$CH_2CONX$ or —$(CH_2)_nY$;

$R^5$ has one of the meanings of $R^4$ with the exception of hydrogen;

$R^6$ denotes ($C_1$–$C_6$)-alkyl or ($C_5$–$C_7$)-cycloalkyl;

$R^7$ and $R^8$ independently of one another denote ($C_1$–$C_4$)-alkyl;

X denotes —$(CH_2)_p$—, —$(CH_2)_2$—O—$(CH_2)_2$— or

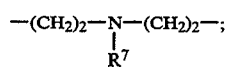

Y denotes —OH, —$OR^7$ or —$NR^7R^8$;

Z denotes aryl or heteroaryl, each of which can optionally also be substituted;

n represents 2, 3 or 4;

m represents 1 or 2; and p represents 4, 5 or 6, and their pharmacologically acceptable acid addition compounds.

The present invention accordingly relates to compounds of the general formula Ia

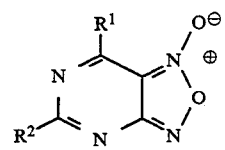

of the general formula Ib

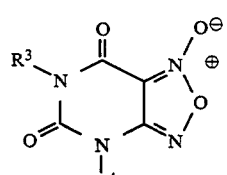

and of the general formula Ic

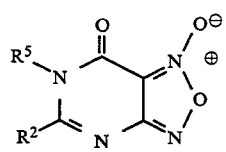

where in each case the radicals $R^1$ to $R^5$ are defined as indicated above.

($C_2$–$C_4$)-, ($C_1$–$C_6$)- or ($C_1$–$C_4$)-alkyl radicals representing $R^3$, $R^4$, $R^5$, $R^6$ and also $R^7$ and $R^8$ can be straight-chain or branched. Examples of alkyl radicals of this type are methyl, ethyl, n-propyl, i-propyl, n-butyl, i-butyl, sec-butyl, tert-butyl and also pentyl and hexyl.

($C_5$–$C_7$)-cycloalkyl representing $R^4$, $R^5$ or $R^6$ is in particular cyclopentyl, cyclohexyl or cycloheptyl.

Aryl representing Z is, in particular, ($C_6$–$C_{14}$)-aryl, phenyl being preferred.

Heteroaryl representing Z is preferably 5- to 7-membered and is derived, for example, from pyrrole or pyridine. α-Pyridyl and β-pyridyl are preferred.

Aryl and heteroaryl representing Z can also be substituted. Suitable substituents are, for example, ($C_1$–$C_4$)-alkyl, ($C_1$–$C_4$)-alkoxy, amino, ($C_1$–$C_4$)-alkylamino, di-($C_1$–$C_4$)-alkylamino, ($C_1$–$C_6$)-alkanoylamino, halogen, preferably fluorine, chlorine or bromine, hydroxyl, nitro or cyano. Aryl or heteroaryl can also be polysubstituted, for example disubstituted or trisubstituted, by the substituents mentioned.

A preferred substituted aryl radical is 3,4-dimethoxyphenyl.

Of the radicals $R^1$, $R^4$ and $R^5$, those are preferred which additionally contain basic or hydrophilic groups. Hydrogen is additionally also preferred for $R^4$.

Particularly preferred $R^1$ radicals are 2-(pyridylmethyl)amino, 3-(pyridylmethyl)amino, 2-hydroxyethylamino, 2-methoxyethylamino, 2-diethylaminoethylamino, 2-(3,4-di-methoxyphenyl)ethylamino, n-butylamino, N,N,di-(hydroxyethyl)amino, N-methylpiperazino and morpholino.

Particularly preferred $R^4$ radicals are hydrogen, methyl, benzyl, ethoxycarbonylmethyl, dimethylaminocarbonylmethyl, morpholinocarbonylmethyl, 2-pyridylmethyl and 3-pyridylmethyl.

Particularly preferred $R^5$ radicals are the particularly preferred $R^4$ radicals with the exception of hydrogen.

$R^2$ preferably denotes hydrogen, methoxy or ethoxy. $R^3$ preferably denotes ethyl.

Very particularly preferred compounds of the general formula I according to the invention are 6-ethyl-[1,2,5]oxadiazolo[3,4-d]pyrimidine-5,7(4H,6H)-dione-1-oxide and 5-methoxy-7-[(3-pyridylmethyl)-amino]-[1,2,5]oxadiazolo[3,4-d]pyrimidine-1-oxide.

Compounds of the general formula Ia according to the invention can be prepared, for example, by reacting compounds of the general formula II

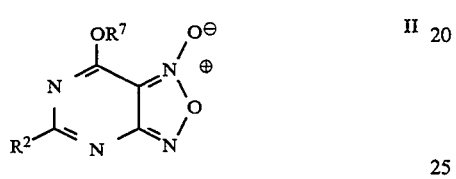

II in which $R^2$ and $R^7$ are defined as indicated above, with amines of the general formula $HR^1$, in which $R^1$ is defined as indicated above. In this reaction, the alkoxy group $-OR^7$ is substituted by the amino group $-R^1$.

The reaction is expediently carried out in an organic solvent or dispersant such as lower alcohols, ethers or esters, preferably in methanol or ethanol. After addition of the stoichiometric amount of the amine, the reaction proceeds at temperatures from 0° to 60° C. The reaction is preferably carried out at 20° to 40° C.

The compounds of the general formula II are either known (for example for $R^2$=H and $R^7$=methyl; Binder et al., Arzneim.-Forsch. 33 (1983) 803; for $R^2$=methoxy and $R^7$=methyl; Nutiu, Boulton, J. Chem. Soc. Perkin Trans. 1, 1976, 1327) or can be prepared analogously to known processes. For example, the compound of the general formula IV can be obtained according to the following scheme from 2,4,6-trichloropyrimidine of the formula III by reaction with two equivalents of an alkali metal alkoxide, and can in turn be nitrated to give the compound of the general formula V. Reaction with hydrazine leads to the compound of general formula VI. This can finally be converted into compounds of the general formula IIa by reaction with sodium nitrite in aqueous hydrochloric acid followed by heating in a solvent such as tetrahydrofuran, chloroform or toluene to 65° to 110° C. with elimination of nitrogen. Alternatively, the compounds of the general formula V can also be reacted directly to give compounds of the general formula IIa by heating with sodium azide in tetrahydrofuran.

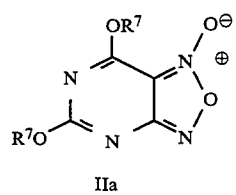

V

VI

IIa

Compounds of the general formula Ib can be obtained, for example, according to the following scheme from compounds of the general formula VII by heating in a high-boiling organic solvent, such as, for example, toluene, xylene, dioxane or dimethylformamide, advantageously in the presence of 10% acetic acid, at temperatures from 90° to 150° C. The compounds of the general formula Ib/1 initially formed here can optionally be converted into compounds of the general formula Ib/2 according to the invention, in which $R^{4'}$ is defined as $R^4$ with the exception of hydrogen, by base-catalysed alkylation with compounds of the general formula $R^{4'}$Hal, in which Hal denotes chlorine, bromine, iodine, mesylate or tosylate.

This alkylation is advantageously carried out in a polar organic solvent such as, for example, tetrahydrofuran, dimethoxyethane, dimethylformamide, dimethyl sulfoxide, methanol, ethanol, acetonitrile or mixtures of these solvents, preferably in tetrahydrofuran or dimethylformamide. Alkali metal hydrides, such as, for example, sodium hydride and lithium hydride, or alkali metal carbonates, such as, for example, potassium carbonate, can be used as base, preferably in a molar amount. The reaction is in general carried out at 40° to 150° C., preferably at 50° to 100° C.

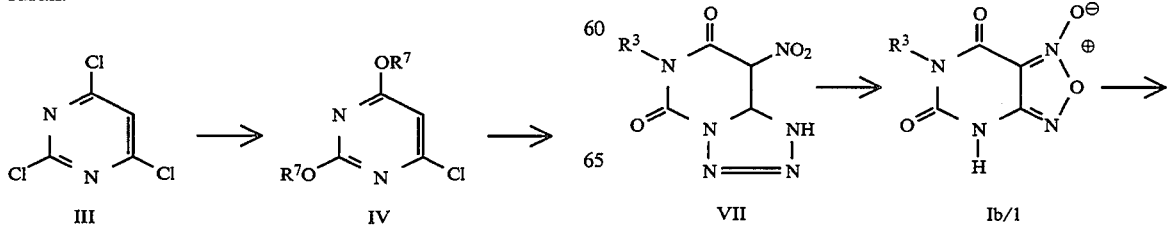

III  IV  VII  Ib/1

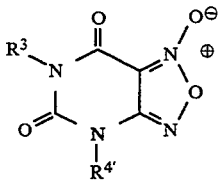

Ib/2

The compounds of the general formula VII can be prepared, for example, by the following routes, which are known in principle:

Starting from 1-alkyl-4-chlorouracils of the general formula VIII (see German Patent 1,139,505), the compounds of the general formula IX are first obtained by nitration, reaction of which with sodium azide yields the nitrotetrazolopyrimidines of the general formula VII (or the corresponding isomeric nitroazidopyrimidines).

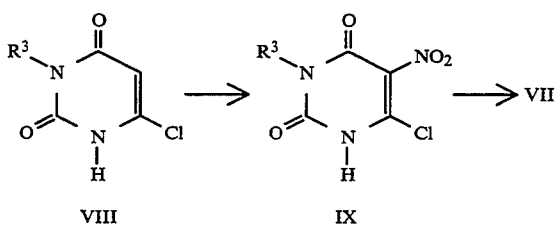

For the synthesis of compounds of the general formula Ib/2, however, the compounds of the general formula VIII can first be reacted to give the 1,3-dialkyl-4-chlorouracils of the general formula X

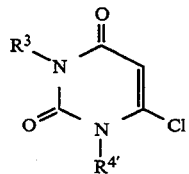

(Pfleiderer et al., Chem. Ber. 111 (1978) 982) and then nitrated as described above, substituted with sodium azide and heated.

Compounds of the general formula Ic can be prepared, for example, from compounds of the general formula XI

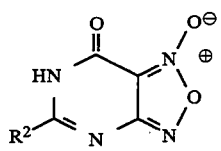

by base-catalysed alkylation with compounds of the general formula $R^5$Hal, in which $R^5$ is defined as indicated above and Hal denotes chlorine, bromine, iodine, mesylate or tosylate.

This alkylation is advantageously carried out in a polar organic solvent such as, for example, tetrahydrofuran, dimethoxyethane, dimethylformamide, dimethyl sulphoxide, methanol, ethanol, acetonitrile or mixtures of these solvents, preferably in tetrahydrofuran. Bases which can be used are alkali metal hydrides, such as, for example, sodium hydride and lithium hydride or alkali metal carbonates, such as, for example, potassium carbonate; lithium hydride is preferred. The reaction is in general carried out at 20° to 150° C., preferably at 20° to 65° C.

The compound of the general formula XI, in which $R^2$ denotes hydrogen, is known and described in Temple et al. J. Org. Chem. 33 (1968) 2086. Corresponding compounds in which $R^2$ represents —$OR^7$ can be prepared from compounds of the general formula XII

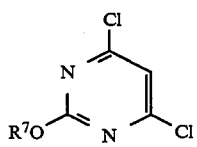

by substitution of a chlorine atom for a hydroxy group, then nitration and reaction with sodium azide.

The compounds of the general formula XII, for their part, can be prepared by reaction of the compound of the formula XIII

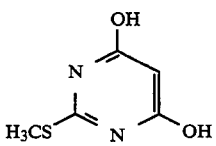

with sodium methoxide and phosphorus oxychloride or from the compound of the formula III using sodium methoxide.

Compounds of the general formula I according to the invention, which contain a basic group in the radicals $R^1$, $R^4$ or $R^5$, can form salts with inorganic or organic acids. Suitable acids for the formation of pharmacologically acceptable acid addition salts are, for example: hydrogen chloride, hydrogen bromide, naphthalenedisulphonic acids, in particular 1,5-naphthalenedisulphonic acid, phosphoric, nitric, sulphuric, oxalic, lactic, tartaric, acetic, salicylic, benzoic, formic, propionic, pivalic, diethylacetic, malonic, succinic, pimelic, fumaric, maleic, malic, sulphamic, phenylpropionic, gluconic, ascorbic, isonicotinic, methanesulphonic, p-toluenesulphonic, citric or adipic acid. The acid addition salts can be prepared in the customary manner by combination of the components, expediently in a suitable solvent or diluent.

The compounds of the general formula I and their pharmacologically acceptable acid addition salts have useful pharmacological properties. In the potassium-depolarised guinea-pig pulmonary artery model, they lead to a relaxation at low concentrations. This action can be inhibited with oxyhaemoglobin, which points to an NO-mediated mechanism. As an activator of guanylate cyclase, nitrogen monoxide leads to an increase in cyclic quanosine monophosphate, which causes a relaxation in the smooth muscle and antiadhesive and antiaggregatory actions in the blood platelets. In addition, nitrogen monoxide is also crucially involved in learning processes, in the regulation of kidney function, in immune defence, in septic shock and in erectile dysfunctions. The compounds of the general formula I and their pharmacologically acceptable acid addition salts can thus be employed in the indications mentioned. Above all, however, NO donors have proven suitable for the treatment and prophylaxis of angina pectoris.

The compounds of the general formula I and their pharmacologically acceptable acid addition salts can therefore be administered to humans as medicines per se, in mixtures with one another or in the form of pharmaceutical preparations which permit enteral or parenteral use and which, as active constituents, contain an effective dose of at least one compound of the general formula I or an acid addition salt thereof, in addition to customary pharmaceutically innocuous excipients and additives.

The medicines can be administered orally, for example in the form of pills, tablets, coated tablets, sugar-coated tablets, hard and soft gelatin capsules, solutions, syrups, emulsions or suspensions, or aerosol mixtures. However, administration can also be carried out rectally, for example in the form of suppositories, or parenterally, for example in the form of injection solutions, or percutaneously, for example in the form of ointments or tinctures.

For the production of the pharmaceutical preparations, pharmaceutically inert inorganic or organic excipients can be used. For the production of pills, tablets, sugar-coated tablets and hard gelatin capsules, lactose, maize starch or derivatives thereof, talc, stearic acid or its salts, etc., for example, can be used. Excipients for soft gelatin capsules and suppositories are, for example, fats, waxes, semi-solid and liquid polyols, natural or hardened oils, etc. Suitable excipients for the production of solutions and syrups are, for example, water, sucrose, invert sugar, glucose, polyols, etc. Suitable excipients for the production of injection solutions are, for example, water, alcohols, glycerol, polyols or vegetable oils.

In addition to the active compounds and excipients, the pharmaceutical preparations can additionally contain additives, such as, for example, fillers, extenders, disintegrants, binders, lubricants, wetting agents, stabilisers, emulsifiers, preservatives, sweeteners, colorants, flavourings or aromatisers, buffer substances, and also solvents or solubilisers or agents for achieving a depot effect, as well as salts for changing the osmotic pressure, coating agents or antioxidants. They can also contain two or more compounds of the general formula I or their pharmacologically acceptable acid addition salts and additionally other therapeutically active substances.

Other therapeutically active substances of this type are, for example: β-receptor blockers, such as, for example, propranolol, pindolol, metoprolol; vasodilators, such as, for example, carbocromene; tranquillisers, such as, for example, barbituric acid derivatives, 1,4-benzodiazepines and meprobamate; diuretics, such as, for example, chlorothiazide; cardiotonic agents, such as, for example, digitalis preparations; hypotensive agents, such as, for example, hydralazine, dihydralazine, ramipril, prazosin, clonidine, Rauwolfia alkaloids; agents which lower the fatty acid level in the blood, such as, for example, bezafibrate, phenofibrate; and agents for thrombosis prophylaxis, such as, for example, phenprocoumon.

The compounds of the general formula I, their pharmacologically acceptable acid addition salts and pharmaceutical preparations which contain the compounds of the general formula I or their pharmacologically acceptable acid addition salts as active compounds can be used in humans in the control or prevention of disorders of the cardiovascular system, for example as antihypertensive medicines in the various forms of high blood pressure, and in the control or prevention of angina pectoris, etc. Moreover, they can also be employed for the treatment of erectile dysfunctions. The dose can vary within wide limits and is to be adjusted to the individual conditions in each individual case. In general, in the case of oral administration a daily dose of about 0.5 to 100 mg, preferably 1 to 20 mg, per human individual is adequate. In the case of other administration forms too, the daily dose, because of the good absorption of the active compounds, is in similar ranges of amounts, i.e. in general also 0.5 to 100 mg/human. The daily dose is normally divided into several, for example 2 to 4, part administrations.

EXAMPLE 1

7-Morpholino-[1,2,5]oxadiazolo[3,4-d]pyrimidine-1-oxide

A solution of 1.6 g (18 mmol) of morpholine in 20 ml of ethanol is added to a mixture of 3.0 g (18 mmol) of 7-methoxy-[1,2,5]oxadiazolo[3,4-d]pyrimidine-1-oxide (Arzneim.-Forsch. 33 (1983) 803) and 100 ml of ethanol. After stirring at room temperature for 4 hours, the solvent is removed by distillation in vacuo and the residue is recrystallised from isopropanol. 3.6 g (90%) of 7-morpholino-[1,2,5]oxadiazolo[3,4-d]pyrimidine-1-oxide are obtained.

M.p. 145°–147° C.

EXAMPLE 2

7-(2-Methoxyethylamino)-[1,2,5]oxadiazolo[3,4-d]pyrimidine-1-oxide

A solution of 1.8 g (24 mmol) of methoxyethylamine in 5 ml of methanol is added dropwise to a suspension of 4.0 g (24 mmol) of 7-methoxy[1,2,5]oxadiazolo[3,4-d]pyrimidine-1-oxide in 120 ml of methanol. The starting material goes into solution and immediately thereafter the product precipitates from the reaction mixture. After 30 minutes, the precipitate is filtered off with suction and washed with methanol. 3.4 g (68%) of 7-(2-methoxyethylamino)-[1,2,5]oxadiazolo[3,4-d]pyrimidine-1-oxide are obtained.

M.p. 135°–137° C. (ethanol)

EXAMPLE 3

7-(2-Diethylaminoethylamino)-5-methoxy-[1,2,5]-oxadiazolo[3,4-d]pyrimidine-1-oxide A mixture of 3.0 g (15 mmol) of 5,7-dimethoxy-[1,2,5]oxadiazolo[3,4-d]pyrimidine-1-oxide (J. Chem. Soc. Perkin Trans. 1, 1976, 1327), 1.75 g (15 mmol) of diethylaminoethylamine and 120 ml of methanol is stirred at room temperature for 2 hours and then concentrated in a rotary evaporator. The residue is dissolved hot in isopropanol, and the solution is filtered and treated with the same amount of hot petroleum ether. Overnight, 2.5 g (59%) of 7-(2-diethylaminoethylamino)-5-methoxy-[1,2,5]oxadiazolo[3,4-d]pyrimidine-1-oxide crystallise out.

M.p. 105°–107° C.

EXAMPLE 4

5-Methoxy-7-(3-picolylamino)-[1,2,5]oxadiazolo[3,4-d]pyrimidine-1-oxide

Analogously to Example 3, 0.75 g (18%) of 5-methoxy-7-(3-picolylamino)-[1,2,5]oxadiazolo[3,4-d]pyrimidine-1-oxide is obtained from 3.0 g (15 mmol)

of 5,7-dimethoxy-[1,2,5]oxadiazolo[3,4-d]pyrimidine-1-oxide and 1.6 g (15 mmol) of 3-picolylamine.

M.p. 136°–138° C.

EXAMPLE 5

6-Ethyl-[1,2,5]oxadiazolo[3,4,-d]pyrimidine-5,7(4H,6H)-dione-1-oxide a) 67.5 g (0.39 mol) of 1-ethyl-4-chlorouracil (German Patent No. 1,139,505) are introduced into 360 g of concentrated sulphuric acid in portions with ice-cooling. 70 ml of fuming nitric acid are added dropwise at 5°–10° C., and the reaction mixture is stirred at 5° C. for 2 hours and then added to 700 g of ice. After stirring for 2 hours, the precipitated product is filtered-off with suction, washed with water and dried in vacuo. 63 g (74%) of 1-ethyl-4-chloro-5-nitrouracil are obtained.

M.p. 182° C.

b) 61.5 g (0.28 mol) of 1-ethyl-4-chloro-5-nitrouracil are heated under reflux for 7 hours With 36.4 g (0.56 mol) of sodium azide in 3500 ml of THF. The mixture is allowed to stand overnight, and the precipitate which deposits (90 g) is filtered off with suction and stirred with 850 ml of acetone for 1 hour. Concentration of the acetone extract yields 53 g (84%) of 6-ethyl-8-nitrotetrazolo-[1,5-c]pyrimidine-5,7(1H,6H)-dione.

c) 20.0 g of 6-ethyl-8-nitrotetrazolo[1,5-c]pyrimidine-5,7(1H,6H)-dione are heated at 120° C. for 7 hours with 200 ml of glacial acetic acid in 2000 ml of xylene. A small undissolved portion is filtered off, the filtrate is concentrated in vacuo and the oily residue is made to crystallise by trituration with methylene chloride. 13.5 g (77%) of 6-ethyl-[1,2,5]oxadiazolo[3,4-d]pyrimidine-5,7(4H,6H)-dione-1-oxide are obtained.

M.p. 141°–142° C.

EXAMPLE 6

6-Ethyl-4-morpholinocarbonylmethyl-[1,2,5]oxadiazolo[3,4-d]pyrimidine-5,7(4H,6H)-dione-1-oxide a) 50 g (0.57 mol) of morpholine are added dropwise at 10° C. to a solution of 58 g (0.28 mol) of bromoacetyl bromide in 500 ml THF. After 2 hours, precipitated morpholine hydrobromide is filtered off, the filtrate is concentrated and the residue is distilled in vacuo at 110° C./0.5 mm Hg. 39 g (67%) of bromoacetyl morpholide are obtained as colourless crystals which melt a little above room temperature.

b) 0.3 g (38 mmol) of lithium hydride is added in portions to a solution of 5.0 g (25 mmol) of 6-ethyl-[1,2,5]oxadiazolo[3,4-d]pyrimidine-5,7(4H,6H)-dione-1-oxide in 150 ml of DMF. The mixture is heated at 60° C. for 30 minutes and a solution of 8.0 g (38 mmol) of bromoacetyl morpholide in 50 ml of DMF is then added dropwise. After a further 90 minutes at 60° C., the DMF is largely removed by distillation in a rotary evaporator, and the residue is treated with water and extracted with ethyl acetate. The ethyl acetate extract is concentrated until it begins to crystallise and 3.0 g (37%) of 6-ethyl-4-morpholinocarbonylmethyl-[1,2,5]oxadiazolo-[3,4-d]pyrimidine-5,7(4H,6H)-dione-1-oxide are obtained.

M.p. 205° C.

EXAMPLE 7

6-Ethyl-4-(3-pyridylmethyl)-[1,2,5]oxadiazolo-[3,4-d]-pyrimidine-5,7(4H,6H)-dione-1-oxide 0.48 g (60 mmol) of lithium hydride is added in portions to a solution of 5.0 g (25 mmol) of 6-ethyl-[1,2,5]oxadiazolo[3,4-d]pyrimidine-5,7(4H,6H)-dione-1-oxide in 250 ml of DMF. The mixture is heated at 60° C. for 15 minutes, then 4.9 g (30 mmol) of 3-picolyl chloride hydrochloride are added and the mixture is heated at 80° C. for 3 hours. It is then largely concentrated, the residue is taken up with ethyl acetate and the mixture is extracted with 10% strength hydrochloric acid. The aqueous extract is neutralised and extracted with ethyl acetate. Relatively readily volatile impurities are removed by distillation in vacuo at 100° C./0.5 mm Hg and the residue is chromatographed. 1.4 g (20%) of 6-ethyl-4-(3-pyridylmethyl)-[1,2,5]oxadiazolo[3,4-d]pyrimidine-5,7(4H,6H)-dione-1-oxide are obtained as a highly viscous oil.

$^{13}$C-NMR (DMSO): δ=12.7 (q), 37.0 (t), 44.1 (t), 101.6 (s), 123.7 (d), 130.7 (s), 135.7 (d), 149.1 (d), 149.2 (d), 149.3 (s), 151.6 (s), 151.6 (s)

EXAMPLE 8

6-Methyl-[1,2,5]oxadiazolo[3,4-d]pyrimidine-7(6H)-one-1-oxide

A solution of 3.0 g (20 mmol) of 7-hydroxy-[1,2,5]oxadiazolo[3,4-d]pyrimidine-1-oxide (C. Temple, C. L. Kussner, J. A. Montgomery, J. Org. Chem. 33 (1968) 2086) in 30 ml of THF is added dropwise to a suspension of 0.18 g (22.5 mmol) of lithium hydride in 20 ml of THF. The mixture is heated at 40° C. for 30 minutes, then 11.5 g (80 mmol) of methyl iodide in 10 ml of THF are added dropwise at room temperature and it is allowed to stand for 2 days. The mixture is diluted with 300 ml of ethyl acetate, washed three times with water, dried over magnesium sulphate and concentrated in vacuo. After recrystallisation from isopropanol, 1.9 g (57%) of 6-methyl-[1,2,5]oxadiazolo[3,4-d]pyrimidine-7(6H)-one-1-oxide are obtained.

M.p. 136°–138° C.

$^{13}$C-NMR (DMSO): δ=33.0 (q), 103.0 (s), 152.0 (s) 155.2 (d), 158.5 (s)

EXAMPLE 9

6-(N,N-Dimethylaminocarbonylmethyl)-[1,2,5]oxadiazolo[3,4-d]pyrimidine-7(6H)-one-1-oxide 4.6 g (30 mmol) of 7-hydroxy-[1,2,5]oxadiazolo[3,4-d]pyrimidine-1-oxide and 0.28 g (35 mmol) of lithium hydride are heated at 50° C. for 30 minutes in 65 ml of THF. A solution of 4.6 g (38 mmol) of 2-chloro-N,N-dimethylacetamide in 10 ml of THF is then added dropwise and the mixture is heated under reflux for 4 hours. The solvent is completely stripped off in a rotary evaporator and the residue is stirred with 30 ml of water for 2 hours. The precipitate is filtered off with suction and recrystallised from THF, and 2.4 g (33%) of 6-(N,N-dimethylaminocarbonylmethyl)[1,2,5]oxadiazolo[3,4-d]pyrimidine-7(6H)-one-1-oxide are obtained.

M.p. 229°–230° C.

The following examples were synthesised analogously to the above working procedures. The structures were confirmed by complete analysis, as well as $^1$H- and $^{13}$C-NMR spectroscopy.

EXAMPLE 10

7-Hydroxyamino-5-methoxy-[1,2,5]oxadiazolo[3,4-d]pyrimidine-1-oxide

M.p. 179° C.

EXAMPLE 11

7-n-Butylamino-5-methoxy-[1,2,5]oxadiazolo[3,4-d]pyrimidine-1-oxide

M.p. 77°–79° C.

EXAMPLE 12

7-(2-Hydroxyethylamino)-[1,2,5]oxadiazolo[3,4-d]pyrimidine-1-oxide
M.p. 117°–119° C.

EXAMPLE 13

5-Methoxy-7-(N-methylpiperazino)-[1,2,5]oxadiazolo[3,4-d]pyrimidine-1-oxide
M.p. 155°–156° C.

EXAMPLE 14

7-(N,N-Di-(2-hydroxyethyl)amino)-5-methoxy-[1,2,5]oxadiazolo[3,4-d]pyrimidine-1-oxide
M.p. 160°–161° C.

EXAMPLE 15

6-Ethyl-4-methyl-[1,2,5]oxadiazolo[3,4-d]pyrimidine-5,7(4H,6H)-dione-1-oxide
M.p. 160°–162° C.

EXAMPLE 16

4-Benzyl-6-ethyl-[1,2,5]oxadiazolo-[3,4-d]pyrimidine-5,7(4H,6H)-dione-1-oxide
M.p. 137°–139° C.

EXAMPLE 17

6-Benzyl-[1,2,5]oxadiazolo[3,4-d]pyrimidine-7(6H)-one-1-oxide
M.p. 165°–170° C.

EXAMPLE 18

6-Morpholinocarbonylmethyl-[1,2,5]oxadiazolo[3,4-d]pyrimidine-7(6H)-one-1-oxide
M.p. 80°–85° C.

EXAMPLE 19

6-Ethoxycarbonylmethyl-[1,2,5]oxadiazolo-[3,4-d]pyrimidine-7(6H)-one-1-oxide
M.p. 163°–165° C.

EXAMPLE 20

5-Methoxy-7-(2-methoxyethylamino)-[1,2,5]oxadiazolo[3,4-d]pyrimidine-1-oxide
M.p. 130°–131° C.

EXAMPLE 21

7-(2-Hydroxyethylamino)-5-methoxy-[1,2,5]oxadiazolo[3,4-d]pyrimidine-1-oxide
M.p. 143°–144° C.

EXAMPLE 22

7-(2-(3,4-Dimethoxyphenyl)ethylamino)5-methoxy-[1,2,5]oxadiazolo[3,4-d]pyrimidine-1-oxide
M.p. 126°–128° C.

EXAMPLE 23

6-(3-Picolyl)-[1,2,5]oxadiazolo[3,4-d]pyrimidine-7-(6H)-one-1-oxide hydrochloride 5.0 g (33 mmol) of 7-hydroxy-[1,2,5]oxadiazolo[3,4-d]pyrimidine-1-oxide and 0.3 g (38 mmol) of lithium hydride are heated at 50° C. for 30 min in 70 ml of THF. After addition of a solution of 5.9 g (46 mmol) of 3-picolyl chloride in 30 ml of DMF, the mixture is heated at 60° C. for 2 h. The solvents are stripped off completely in a rotary evaporator, and the residue is digested several times with THF. The product is precipitated from the combined THF extracts by addition of ethereal hydrochloric acid and recrystallised from methanol. 1 g of 6-(3-picolyl)-[1,2,5]oxadiazolo[3,4-d]pyrimidine-7(6H)-one-1-oxide hydrochloride is obtained.
M.p. 205°–207° C.

It is to be understood that the above described embodiments of the invention are illustrative only, and that modifications thereof may occur to those skilled in the art. Accordingly, this invention is not to be regarded as limited to the embodiments disclosed herein, but is to be limited only as defined by the appended claims.

We claim:
1. Pyrimidofuroxans of the formula I

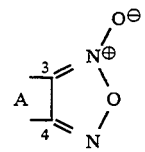

in which
A denotes

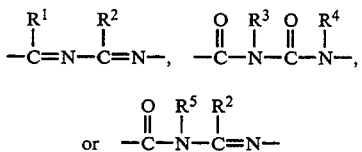

where in each case the nitrogen atom is bonded via C-4 and the carbon atom is bonded via C-3 of the furoxan ring;

$R^1$ denotes —$NHR^6$, —$NR^7R^8$, —NX, —NHOH, —$NH(CH_2)_nY$, —$N[(CH_2)_nY]_2$ or —$NH(CH_2)_mZ$;

$R^2$ denotes hydrogen or —$OR^7$;

$R^3$ denotes ($C_2$–$C_4$)-alkyl;

$R^4$ denotes hydrogen, ($C_1$–$C_6$)-alkyl, ($C_5$–$C_7$)-cycloalkyl, —$CH_2Z$, —$CH_2COOR^7$, —$CH_2CONR^7R^8$, —$CH_2CONX$ or —$(CH_2)_nY$;

$R^5$ has one of the meanings of $R^4$ with the exception of hydrogen;

$R^6$ denotes ($C_1$–$C_6$)-alkyl or ($C_5$–$C_7$)-cycloalkyl;

$R^7$ and $R^8$ independently of one another denote ($C_1$–$C_4$)-alkyl;

X denotes —$(CH_2)_p$—, —$(CH_2)_2$—O—$(CH_2)_2$— or

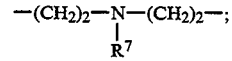

Y denotes —OH, —$OR^7$ or —$NR^7R^8$;
Z denotes aryl or heteroaryl, each of which can optionally also be substituted;
n represents 2, 3 or 4;
m represents 1 or 2; and
p represents 4, 5 or 6,
and their pharmacologically acceptable acid addition compounds.

2. Pyrimidofuroxans according to claim 1, characterised in that $R^1$ denotes 2-(pyridylmethyl)amino, 3-(pyridylmethyl)amino, 2-hydroxyethylamino, 2-methoxyethylamino, 2-diethylaminoethylamino, 2,(3,4-dimethoxyphenyl)ethylamino, n-butylamino, N,N-di-(2-hydroxyethyl)amino, N-methylpiperazino or morpholino.

3. Pyrimidofuroxans according to claim 1, characterised in that $R^2$ denotes hydrogen, methoxy or ethoxy.

4. Pyrimidofuroxans according to claim 1, characterised in that $R^3$ denotes ethyl.

5. Pyrimidofuroxans according to claim 1, characterised in that $R^4$ denotes hydrogen, methyl, benzyl, ethoxycarbonylmethyl, dimethylaminocarbonylmethyl, morpholinocarbonylmethyl, 2-pyridylmethyl or 3-pyridylmethyl.

6. Pyrimidofuroxans according to claim 1, characterised in that $R^5$ denotes methyl, benzyl, ethoxycarbonylmethyl, dimethylaminocarbonylmethyl, morpholinocarbonylmethyl, 2-pyridylmethyl or 3-pyridylmethyl.

7. Pharmaceutical preparation, characterised in that it contains a pyrimidofuroxan of the formula I according to claim 1, or a pharmacologically acceptable acid addition salt thereof as active compound together with pharmaceutically acceptable excipients and additives and, optionally, one or more other pharmacological active compounds.

8. Process for the treatment of disorders of the cardiovascular system, which comprises administering effective amounts of a pyrimidofuroxan of formula I according to claim 1, or a pharmacologically acceptable acid addition compound thereof, to a patient in need thereof.

9. Process according to claim 8 in which the disorder of the cardiovascular system is angina pectoris.

10. Process according to claim 8 in which the disorder of the cardiovascular system is erectile dysfunction.

* * * * *